United States Patent [19]

Hoffman et al.

[11] Patent Number: 5,356,777
[45] Date of Patent: Oct. 18, 1994

[54] METHODS OF DETECTING PERIODIC PARALYSIS IN HORSES

[75] Inventors: Eric P. Hoffman, Pittsburgh, Pa.; Sharon J. Spier, Winters, Calif.; Jeffrey A. Rudolph, Pittsburgh, Pa.; Glen Byrns; Domenico Bernoco, both of Davis, Calif.

[73] Assignee: University of Pittsburgh, Pittsburgh, Pa.

[21] Appl. No.: 954,830

[22] Filed: Oct. 1, 1992

[51] Int. Cl.$^5$ .................. C12Q 1/68; C12P 19/34; C07H 21/02; C07H 21/04
[52] U.S. Cl. .................... 435/6; 435/91.1; 435/91.2; 536/23.1; 536/24.3; 536/24.31; 536/24.33; 935/77; 935/78; 935/19
[58] Field of Search ............ 435/6, 91, 91.1, 91.2, 435/77, 78, 19; 536/18.7, 23.1, 24.3, 24.33

[56] References Cited

PUBLICATIONS

Noda et al. Nature 320:188 (1986).
Kayano et al. FEB Lett 228(1):187 (1988).
Wang et al. Biochem. Bioph. Res. Comm. 182(2) (1992).
Trimer et al. Neuron 3:33 (1989).
Kallen et al. Neuron 4:233 (1990).
Rudolph, et al. Nature Genet. 2:144 (1992).
Cunningham, P., Sci. Am. 92 (May, 1991).
Holden, C., Science 252:34 (1991).
Leipold, H. W., et al., Large Animal Internal Medicine (Ed. Smith, B. P.) 1567 (E. V. Mosby Co., St. Louis) (1990).
Spier, S. J., et al., J. Am. Vet. Assoc. 197:1009 (1990).
Fontaine, B., et al., Science 250:1000 (1990).
Koch, M. C., et al., Hum. Genet. 88:71 (1991).
Ptacek, L. H., et al., Am. J. Hum. Genet. 49:851 (1991).
Rojas, C. V., et al., Nature 354:387 (1991).
Ptacek, L. J. et al., Cell 67:1021 (1991).
Ptacek, L. J., et al., Neuron 8:891 (1992).
McClatchey, A. I., et al., Cell 68:769 (1992).
Spier, S. J., et al., J. Am. Vet. Med. Assoc. 202(6):993 (1993).
Pickar, J. G., et al., Am. J. Physiol. (Cell Physiol.) 260 C926 (1991).
Rudolf, J. A., et al., Animal Genetics 23:241 (1992).

Primary Examiner—Margaret Parr
Assistant Examiner—Migual Escallon
Attorney, Agent, or Firm—Reed Smith Shaw & McClay

[57] ABSTRACT

Methods for detecting the mutation in the horse adult skeletal muscle sodium channel alpha-subunit gene that causes hyperkalaemic periodic paralysis in horses is provided based on a mutation in the sodium channel region IV, $S_3$.

13 Claims, 3 Drawing Sheets

Transmembrane domain IV-$S_3$

```
Human-A Muscle      VGWNI F DFVVVILSIVGLALSDLI
Rat-A Muscle        IGWNI F DFVVVILSIVGLALSDLI
Rat-F Muscle        NSWNI F DFVVVILSIVGTVLSDII
Rat Brain I         IGWNI F DFVVVILSIVGMFLAELI
Rat Brain II        IGWNI F DFVVVILSIVGMFLAELI
Rat Brain III       IGWNI F DFVVVILSIVGMFLAELI
Drosophila para 1   EPWNL F DVVVVILSILGLVLSDII
Eel electroplax     VGWNV F DFAVVVISIIGLlLSDII
Horse-A Muscle      VGWNI F DFVVVILSIVGLALSDLI
HYPP Horse          VGWNI L DFVVVILSIVGLALSDLI
```

METHODS OF DETECTING PERIODIC PARALYSIS IN HORSES

The present invention was developed in part with government support under grant number AR41025 (EPH) awarded by the National Institutes of Health. The government has certain rights in this invention.

FIELD OF THE INVENTION

The present invention relates generally to a genetic disease observed in horses called hyperkalaemic periodic paralysis (HYPP). In particular the invention relates to the discovery of the genetic mutation that causes HYPP and methods for diagnosis of the disease.

BACKGROUND OF THE INVENTION

Selective breeding for desirable traits is an established practice in animal husbandry. Form, function, and fashion have contributed to the popularity of certain sires of bloodlines in various breeds of horses.

As horses are selected for their athletic abilities, for instance, racing speed or gait, less desirable traits can be expanded in the equine gene pool. The genetic consequences of such intensive selective inbreeding of popular lines of horses have received attention recently. See, for example, Cunningham, P., *Sci. Am.* 92 (May, 1991), and Holden, C., *Science* 252:34 (1991), the disclosures of which are incorporated herein by reference. Such purposeful breeding of popular horses has resulted in a disproportionate representation of a small number of sires in the ancestry of all extant horses. In the example of Thoroughbreds, only four stallions are responsible for 30% of the current gene pool. Cunningham, P., *Sci. Am.* 92 (May, 1991). Diseases of horses with proven or probable genetic basis include HYPP, combined immunodeficiency disease of Arabian horses, cerebellar abiotrophy, osteochondrosis, and equine degenerative myeloencephalopathy, among others. See, Leipold, H. W., et al., *Large Animal Internal Medicine* (Ed. Smith, B. P.) 1567 (E. V. Mosby Co., St. Louis) (1990), the disclosure of which is incorporated herein by reference.

Quarter Horses are the most popular breed of horses in the United States and were originally bred in the 1600's to run the quarter mile. Pronounced muscularity is a desirable trait in Quarter Horses and is frequently mentioned in the American Quarter Horse Association description of the breed. Recently a sire possessing particularly well developed musculature contributed substantially to the genetic makeup of the 2.9 million Quarter Horses that are currently registered. Concurrently with the rise in popularity of this sire, HYPP, an autosomal dominant disease characterized by potassium-induced episodes of skeletal muscle paralysis has been frequently found in Quarter Horses. See, Spier, S. J., et al., *J. Am. Vet. Med. Assoc.* 197:1009 (1990), the disclosure of which is incorporated herein by reference. All affected horses have been traced back to this common ancestor.

HYPP in humans is also inherited as an autosomal dominant trait and ha s been extensively studied. The human disease is characterized by intermittent attacks of weaknesses or paralysis. Both HYPP and paramyotonia congenita, a clinically distinct dominant disorder typified by cold-induced involuntary muscle contraction (myotonia), have been shown to have been linked to the human adult skeletal muscle sodium channel gene on chromosome 17 g. See, Fontaine, B., et al, *Science* 250:1000 (1990); Koch, M. C., et al., *Hum. Genet.* 88:71 (1991); and Ptacek, L. H., et al., *Am. J. Hum. Genet.* 49:851 (1991), the disclosures of which are incorporated herein by reference. Recently, mutations of the human sodium channel have been identified for both HYPP as reported by Rojas, C. V., et al., *Nature* 354:387 (1991) and Ptacek, L. J., et al., *Cell* 67:1021 (1991), the disclosures of which are incorporated herein by reference, and paramyotonia congenita as reported by Ptacek, L. J., et al., *Neuron* 8:891 (1992), and McClatchey, A. I., et al., *Cell* 68:769 (1992), the disclosures of which are incorporated herein by reference. All of these mutations cause single amino acid substitutions that affect sodium channel functions.

Because of the clinical, genetic, and electrophysiological similarities between the human disease and HYPP in Quarter Horses it has been suggested that they could represent homologous disorders. For example, both show fully penetrant dominant inheritance as described by Spier, S. J., et al., *J. Am. Vet. Med. Assoc.* (In press) 202:993 (1993), the disclosure of which is incorporated herein by reference, potassium-induced attacks as described by Ptacek, L. J., et al., *Neuron* 8:891 (1992), the disclosure of which is incorporated herein by reference, elevated serum potassium during attacks, and membrane potential abnormalities in isolated muscle cells as described by Pickar, J. G., et al., *Am. J. Physiol. (Cell Physiol.)* 260, C926 (1991), the disclosures of which are incorporated herein by reference.

In order to test this hypothesis a molecular genetic linkage study was conducted by Rudolf, J. A., et al., *Animal Genetics* 23:241 (1992), the disclosure of which is incorporated herein by reference, in part of a large HYPP Quarter Horse pedigree using a polymerase chain reaction (PCR)-based polymorphism that was discovered while horse sodium channel α-subunit cDNA was being sequenced. The study revealed no recombinants between this particular polymorphism and the trait in ten informative meioses (LOD $Z=2.7$; $\theta=0$). The analysis indicated that the sodium channel alpha subunit was a likely candidate gene for HYPP in Quarter Horses.

Horses affected with HYPP exhibit episodes of weakness and collapse which pose a hazard to themselves and their riders. Since affected horses usually do not exhibit signs of the disease until they are mature and in training, breeders and sellers of young horses often do not know if offspring of affected horses carry the trait. At the present time known methods of testing for HYPP are inadequate, such as, potassium chloride challenge which can lack sensitivity and spontaneous activity by electromyography which is not specific for HYPP. Therefore there is a need for a realiable and accurate diagnostic test to diagnose this disease and help eliminate this disease from horses.

The present invention provides the identification of the mutation that causes HYPP in horses and methods of diagnosing the HYPP disease by detecting or identifying the mutation.

SUMMARY OF THE INVENTION

Accordingly it is a primary object of the present invention to identify the genetic mutation that cases periodic paralysis (HYPP) in horses.

Another object of the present invention is to provide methods for accurate diagnosis of HYPP in horses at the molecular level.

Yet another object of the present invention is to provide methods for accurate diagnosis of HYPP in horses prenatally and post mortem, as well as during the life of the horse.

These and other objects of the present invention are achieved by one or more of the following embodiments.

In one aspect, the invention features a method for detecting the genetic mutation in horses that causes hyperkalaemic periodic paralysis wherein said mutation is in the horse adult skeletal muscle sodium channel gene, domain IV, segment $S_3$.

In another aspect, the invention features a method of detecting the mutation in the horse adult skeletal muscle sodium channel gene that causes hyperkalaemic periodic paralysis, comprising:

obtaining genomic DNA or RNA from a prenatal, living, or deceased horse;

amplifying the genomic DNA or reverse transcribed RNA by polymerase chain reaction to obtain an amplification product that includes part of the horse adult skeletal muscle sodium channel gene defined as domain IV segment $S_3$; and analyzing said product for said mutation.

In a preferred embodiment, the invention features oligonucleotide probes which comprise:

Normal Horse: 5'-AACATCTTCGACTTCGT (SEQ ID NO: 1) and

HYPP Horse: 5'-AACATCTTGGACTTCGT (SEQ ID NO: 2).

Other features and advantages of the invention will be apparent from the following description of the preferred embodiment, and from the claims.

DETAILED DESCRIPTION OF THE INVENTION

The present invention may be used to detect the presence or absence of the gene that causes HYPP in horses. Samples of DNA or RNA analyzed by the methods of the present invention may be obtained from prenatal, living, or deceased horses.

I. Definitions

As used herein, the terms "mutation" and "HYPP horse mutation" refer to a single base change in the horse adult skeletal muscle sodium channel α subunit gene, which change is from phenylalanaine in a normal horse to leucine in a horse affected with HYPP in domain IV, transmembrane region/segment $S_3$ of the horse adult skeletal muscle sodium channel gene, as described herein.

"Disease" refers to hyperkalemic periodic paralysis.

"Affected" or "HYPP-affected" refer to horses having hyperkalemic periodic paralysis, a dominantly inherited genetic condition of horses which shows attacks of weakness and/or fasciculations which can be induced by potassium ingestion or injection.

The terms "normal" or "nonaffected" refer to horses which do not have hyperkalemic periodic paralysis.

"Horse" is any animal of the family equidae including, but not limited to, horses, asses, quagga, and zebras.

II. Methods

Horse Breeding

Figure 1:
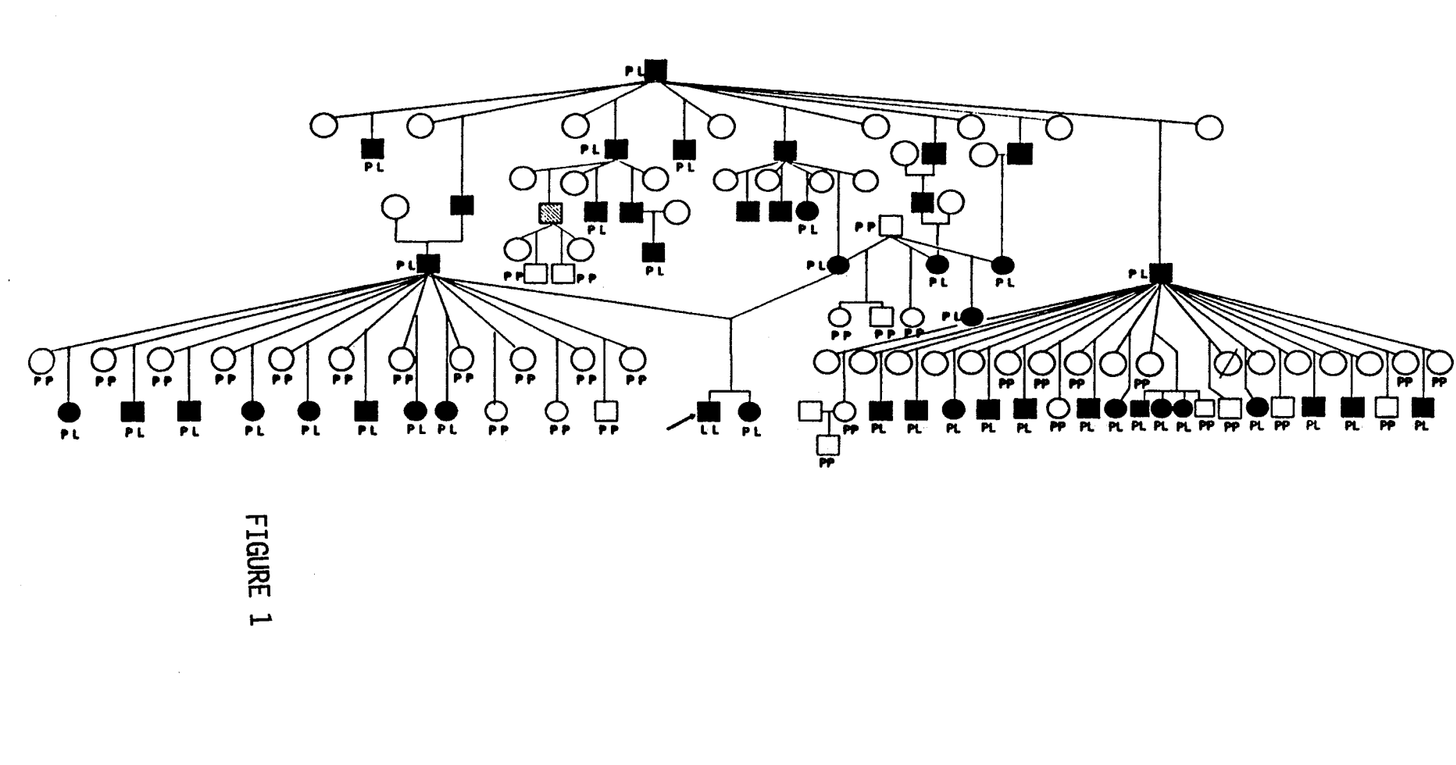
FIG. 1 is a diagram of an HYPP Quarter Horse pedigree that was analyzed for HYPP using the methods of the present invention. Horses shown are typed for the normal allele (PP) of the adult skeletal sodium channel α subunit gene (phenylalanine (P)) and the allele (PL) believed to cause HYPP (leucine (L)) The affected horse homozygous for the Leu mutation (LL) is indicated by an arrow and the hatched horse has an unknown affected status.

Controlled horse breedings were done at the Equine Research Center, University of California, Davis, Calif. 53 horses were bred. Other horses included in the study were referred from other breeders. All of the horses were either tested for HYPP status by means of high dose potassium challenge or were reported to have clinical signs associated with increased serum K+ or had a history of repeated episodes of muscular fasciculation. A total of 227 horses were studied. The Quarter Horse pedigree analyzed using the methods of the present invention is shown diagrammatically in FIG. 1.

Identification of Sodium Channel Mutation

In order to identify the putative mutation, muscle biopsies of normal and affected horses were analyzed by cross-species PCR mediated cDNA cloning and sequencing performed according to the methods of Rudolf, J. A., et al., *Animal Genetics* 23:241 (1992), the disclosure of which is incorporated herein by reference. Additionally, single strand conformational polymorphism (SSCP) analysis of the reverse transcribed PCR (RT-PCR) products was carried out according to the protocol of Orita, M., et a., *Proc. Nat. Acad. Sci.* 86:2766 (1989), and Ptacek, L. J., et al., *Neuron* 8:891 (1991), the disclosures of which are incorporated herein by reference.

Muscle biopsies were obtained from an HYPP-affected horse and 2 normal horses. RNA was isolated and reverse transcribed into a cDNA strand using an avian reverse transcriptase (Life Sciences, Inc., Gainsville, Fla.) using an oligo dT primer (Pharmacia, Piscatawa, N.J.). Single-stranded cDNA was synthesized from purified RNA using DNA polymerase I. The resulting muscle cDNA was used as a template for the polymerase chain reaction (PCR). RNA preparation from the muscle biopsies, cDNA synthesis and PCR were performed as described by Rojas, C. V., et al., *Nature* 354:387 (1991), the disclosure of which is incorporated herein by reference. The rat sodium channel sequence described by Trimmer, J., S., et at., *Neuron* 3:33 (1989) and the human sodium channel sequence as described by Wang, J., et al., *Biochem, Biophys. Res. Common.* 182:794 (1992), the disclosures of which are incorporated herein by reference, were used to design the primers used for all the PCR amplifications. Restriction sites were built into the primers permitting directional cloning. The primers used for PCR amplification were:

Horse IVS$_2$F4: 5'-GGGGAGTGTGTGCT-CAAGATG (SEQ ID NO: 3) and

Horse IVS$_3$R: 5'-AATGGACAGGATGACAAC-CAC (SEQ ID NO: 4).

The Phe to Leu mutation was found in the affected horse in the region amplified by these primers.

SSCP gel analysis was performed on the amplified cDNA as described by Ptacek, L. J., et al., *Cell* 67:1021 (1991) for 68% of the horse 5.5 kb coding sequence for the adult skeletal muscle sodium channel α subunit gene. The oligonucleotide probes for performing differential allele-specific oligonucleotide hybridization (ASOH) were as follows:

Normal Horse: 5'-AACATCTTCGACTTCGT (SEQ ID NO: 1) and

HYPP Horse: 5'-AACATCTTGGACTTCGT (SEQ ID NO: 2).

The oligonucleotide probes for allele-specific oligonucleotide hybridization or other hybridization methods that can detect the HYPP mutation may be synthesized according to methods well known in the art and labeled with any label that can be detected such as radionuclides such as $^{32}p$, or colorimetric enzymes.

Figure 2A:
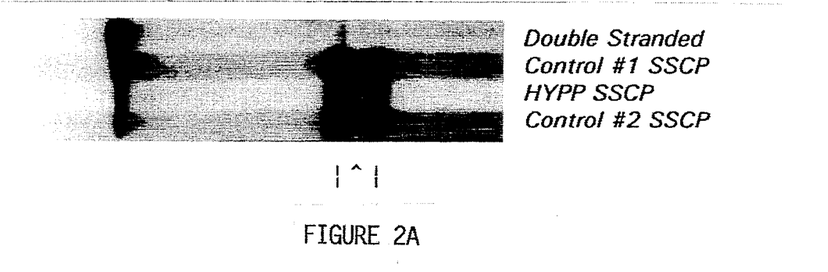
FIG. 2A is a photograph of an autoradiogram directly visualized by $^{32}p$ of single strand conformational polymorphism (SSCP) gel analysis of single-stranded conformers of reverse transcribed horse muscle RNA in the amino acid region 1358–1514 (using rat sequence numbers) of the horse adult skeletal sodium channel α subunit gene that were amplified by polymerase chain reaction (PCR). Lane 1 contains double stranded PCR product; lanes 2 and 4 contain normal horse single stranded PCR product as a control; and lane 3 contains single stranded PCR product from an affected horse. The sign (<) indicates the unique conformer that shows that this region of the diseased horse contains a possible mutation.

A single-strand conformer specific for an affected horse was seen in PCR products covering the amino acid region 1279-1514 and also in the overlapping region 1348-1514. SSCP gel analysis was performed on the single-stranded conformers of reverse transcribed PCR products (RT-PCR products) of horse muscle RNA in the amine acid region 1348-1514 (using rat sequence numbers). The results are shown in FIG. 2A. Lane 1 contained double stranded PCR product, lanes 2 and 4 contained normal horse single stranded PCR product as controls, and lane 3 contained single stranded PCR product from an affected horse. The results of the SSCP analysis revealed a conformer (central arrow) from the affected horse that is not seen in normal horses.

In order to determine the sequences of the regions from both normal horse muscle and affected horse muscle that showed the disease specific conformer, these regions were cloned into M13mp18 and M13mp19 vectors (Boehringer Mannheim, Indianapolis, Ind.) according to manufacturer's protocols. As shown in the FIG. 2B nucleotide sequence analysis and amino acid sequence analysis of the 1358–1514 region a C to G transversion (right panel) (SEQ ID NO: 7 and SEQ ID NO: 8, respectively) was present in 5 out of 18 sequenced clones from the affected horse. 20 HYPP phage isolates, and 4 normal horse phage isolates were sequenced enzymatically using dideoxy chain termination procedures with $^{35}$S-dATP, using the sequence kit and protocol of U.S. Biochemicals, Inc.

In order to determine whether there were mutations in the rest of the coding sequence of the horse sodium channel gene, sequencing of approximately 10 RT-PCR clones was performed for 44% of affected and unaffected horse coding sequence as described above using the primers designed from the rat and human sodium channel sequence. 68% of the coding sequence was screened by SSCP, for a total of 84% of cDNA screened. 16% of the coding sequence was not analyzed by either method.

Figure 2B:
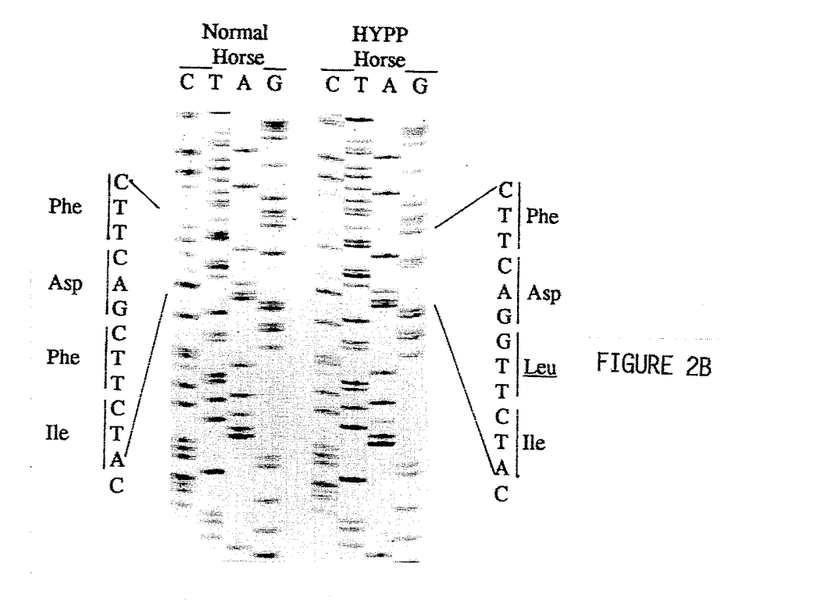
FIG. 2B is a photograph of an autoradiogram visualized by $^{32}p$ of a sequencing gel showing nucleotide sequence analysis and amino acid sequence analysis of part of the 1358–1514 region of the adult skeletal muscle sodium channel α subunit gene from a normal horse (left) (SEQ ID NO: 5 and SEQ ID NO: 6, respectively), and nucleotide sequence analysis and amino acid sequence analysis of the same region of an affected horse (right)(SEQ ID NO: 5 and SEQ ID NO: 6, respectively) showing a C to G transversion that is consistent with the conformer shown in FIG. 2A.
Figure 2C:
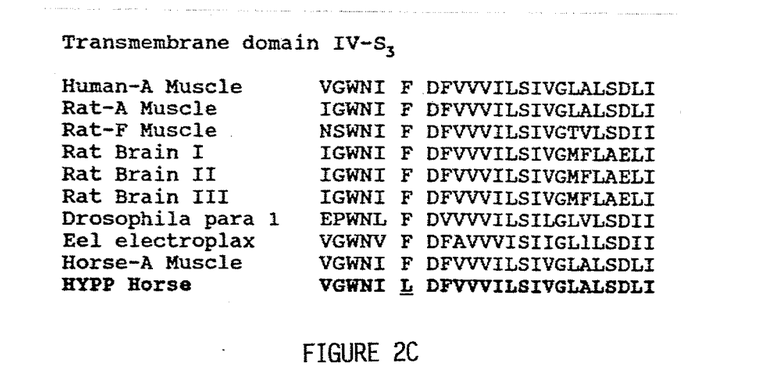
FIG. 2C shows an amino acid sequence alignment of sequenced sodium channel α subunits over the $IVS_3$ region of different species and the same region of an HYPP horse.

FIG. 2C shows the amine acid sequence alignment of the domain IV, S$_3$ region was compared with human adult skeletal muscle (human-A muscle), rat adult skeletal muscle (rat-A muscle), rat fetal skeletal muscle (rat-F muscle), Kallen, R. G., et al., *Neuron* 4:233 (1990); rat brain I; rat brain II; rat brain III; drosphilia para 1; eel electroplax, Noda, M., et al., *Nature* 312:1212, (1984); and horse A-muscle. The Phe residue is conserved in all species studied but is changed in the HYPP horse channel.

The C to G change is predicted to substitute a leucine residue for a phenylalanine residue as shown by the identification of a disease-specific conformer in SEQ ID NO: 8 in FIG. 2B. All muscle and brain sodium channel alpha subunits sequenced to date show a phenylalanine in the analogous position as seen in FIG. 2C. This finding strongly suggests evolutionary conservation and therefore a functional significance of this phenylalanine residue.

Genotyping of Horse HYPP Mutation 227 horses were typed for the C to G mutation by allele-specific oligonucleotide hybridization to PCR amplified genomic DNA. Genomic DNA was extracted from peripheral blood using either the salting out procedures of Miller, S. A., et al., *Nuc . Acids. Res.* 16:1215 (1988), the disclosure of which is incorporated herein by reference, or the proteinase K/non-ionic detergent procedure of Higuchi, R., *Amplifications-A Forum for PCR Users* (Issue 2) Cetus Corporation, Norwalk, Conn., the disclosure of which is incorporated herein by reference. PCR amplification of genonic DNA was carried out with approximately 1 μg DNA and Horse IVS$_2$F4 (SEQ ID NO: 3) and Horse IVS$_3$R (SEQ ID NO: 4) primers that flank the polymorphism as set forth above, using GeneAmp kits (Cetus Corp., Norwalk, Conn.). After amplification, the PCR products were phenol/ chloroform extracted and precipitated with ethanol.

The amplified samples of normal and affected horses were analyzed by restriction fragment length polymorphism (RFLP) analysis via a Taq I assay followed by polyacrylamide gel electrophoresis (PAGE) analysis. The Taq I enzyme cuts the TCGA sequence in PCR product that contains the phenylalanine codon found in unaffected horses into two DNA fragments of 64 and 28 base pairs. PCR products containing the mutant leucine codon (TGGA) are not recognized by the restriction enzyme and remains undigested. Therefore, products from horses showing complete digestion of the PCR product at this site into two fragments are normal horses unaffected by HYPP. Those horses that showed equal proportions of digested products (64 and 28 bp in length) and undigested products (92 bp in length) were heterozygous (Phe/Leu) affected horses and were affected with HYPP. PCR products from that were not digested at all were from homozygous (Leu/Leu) horses that were also affected with the disease. The digestion products were then analyzed by PAGE.

In addition to Taq I, any restriction enzyme that recognizes the normal and HYPP adult skeletal muscle sodium channel gene differently from any other DNA or RNA sample may be used for RFLP analysis.

Samples were digested with Taq I (Boehringer Mannheim) according to the protocol provided by the manufacturer. The digested samples were then run on 1% Sea Kem, 2% NuSeive gels (Seakem, Inc., Place) or electrophoresed on 6% acrylamide/TBE native gels.

The distribution of affected and normal horses according to the three expected genotypes is shown below in Table 1.

TABLE 1

| Type | Phe/Phe | Phe/Leu | Leu/Leu | Totals |
|------|---------|---------|---------|--------|
| Affected | 0 | 49 | 2 | 51 |
| Normal | 176 | 0 | 0 | 176 |
| Totals | 176 | 49 | 2 | 227 |

As seen in Table 1, all 176 normal horses were homozygous for the normal allele (Phe/Phe), which does not suggest linkage disequilibrium with some other mutation. Additionally, 84% of the horse sodium channel cDNA which was sequenced or analyzed by SSCP as described above, did not reveal any additional conformers which would have indicated any additional base changes in affected horses. Thus, the allele distribution, SSCP analysis, and evolutionary conversation data all strongly suggest that the phenylalanine to leucine change causes HYPP in Quarter Horses.

Allele-specific oligonucleotide hybridization was also used to determine the presence of the HYPP mutation and the genotype of particular affected and nonaffected horses. Genomic DNA was obtained as described above from a founding sire for the left half of the horse pedigree in FIG. 1 (Horse 1); dams mated with this sire (Horses 2, 4, and 7) and offspring from these matings (Horses 3,5, and 6). The genomic DNA was amplied by PCR using the methods and Horse IVS$_2$F4 (SEQ ID NO: 3)and Horse IVS$_3$R (SEQ ID NO: 4) primers described above. Briefly, 30 cycles of PCR at 94° C. for 1 minute then at 65° C. for 4 minutes as carried out. The resulting PCR products were visualized by ethidium bromide staining of 1% agarose 2% NuSeive agarose mixed gels, then roughly equal amounts were denatured and slot-blotted onto nylon membranes. Membranes were baked and processed for differential hybridization with oligonucleotides. Oligonucleotides used for differential hybridization were the Normal Horse (SEQ ID NO: 1) and HYPP Horse (SEQ ID NO: 2) oligonucleotide probes described above.

The oligonucleotide probes were desalted on NAP-10 columns, and 10 pmol were end-labelled using T4 polynucleotide kinase and $\gamma$-$^{32}$P-labelled ATP (10 pmol of 6,000 Ci mmol$-^1$). Labelling reactions were used directly for hybridization. Duplicate filters were washed at high stringency (0.1×SSC, 0.5% SDS; at 49° C.), see, Rojas, C. V., et al., Cell 67:1021 (1991), the disclosure of which is incorporated herein by reference, autoradiographed, and the signals compared.

Figure 3:
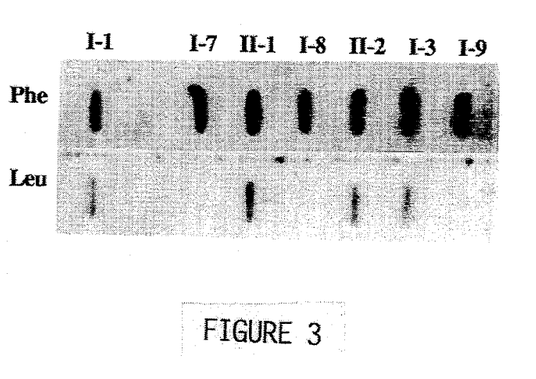
FIG. 3 is a photograph of an autoradiogram visualized by $^{32}p$ showing results of allele-specific oligonucleotide hybridization performed on PCR products from genomic DNA obtained from seven horses from the horse pedigree illustrated in FIG. 1 with labeled oligonucleotide probes. The numbers correspond to 1)-a founding sire for the left half of the horse pedigree in FIGS. 1; 2, 4, and 7)-dams mated with this sire; and 3, 5 and 6)-offspring from these matings. Horses 2, 4, and 7 are normal and homozygous for the normal (Phe) allele while horses 1, 3, 5, and 6 are affected and heterozygous, having both a normal allele and one with the HYPP leucine allele (Leu).

The results of this ASOH analysis in FIG. 3 show that hybridization of the gamma-$^{32}$P-labeled HYPP horse probe hybridized to PCR products from heterozygous horses affected with HYPP. Thus horses 1, 3, 5, and 6 were affected with HYPP and heterozygous, having both a normal allele and one with the HYPP leucine allele (Leu). Horses 2, 4, 7 were normal and homozygous for the normal (Phe) allele In order to determine whether the leucine substitution co-segregates with the HYPP disease allele-specific oligonucleotide hybridization and/or Taq I restriction analysis of PCR-amplified genomic sequences was carried out to study the extended pedigree shown in FIG. 1.

All affected horses in this pedigree possessed the leucine substitution and all unaffected horses possessed the phenylalanine residue which were determined using either Taq I digestion of PCR products or ASOH analysis using the PCR primers denoted as Horse IVS$_2$F4 (SEQ ID NO: 3) and Horse IVS$_3$R (SEQ ID NO: 4) above; probes used were the "Normal Horse (SEQ ID NO: 1)" and "HYPP Horse" (SEQ. ID NO: 2) probes described above. Additionally, 8 horses which were uninformative in the original linkage analysis showed complete agreement with the amino acid residue substitution and the disease (LOD Z=7.22, $\theta$=0).

Sequence Comparisons of HYPP and Normal Horses

As discussed above, a total of 51 affected Quarter Horses, all descending from a common sire were studied and all were found to possess the phenylalanine to leucine change. It was possible, however, that this change was in strong linkage disequalibrium with the disease-causing mutation and was therefore a polymorphism. To determine whether this was the case, 176 unaffected horses from a variety of breeds were typed using Taq I digestion of PCR products or ASOH analysis of PCR products. Diagnosis of the affected horses was established on the basis of clinical signs associated with increased serum K+ or a history of repeated episodes of muscular fasciculation. Genomic DNA samples were amplified using the Horse IVS$_2$F4 (SEQ ID NO: 3) and Horse IVS$_3$R (SEQ ID NO: 4)primers described above and the amplified samples were digested with the restriction enzyme Taq I as described previously. Polyacrylamide gel electrophoresis (PAGE) analysis was carried out which revealed two DNA fragments of 64 and 28 bp in normal horses. Heterozygous affected horses showed an additional fragment of 92 bp, while homozygous affected animals had two 92 bp fragments.

No homozygotes for dominant sodium channel mutations have been previously described in humans or other animals. One of the horses in the pedigree was a possible homozygote for the disease as suggested by the previous linkage analysis shown in FIG. 1 and indicated therein by an arrow. Allele-specific hybridization confirmed that this horse is a homozygote, as was another horse in a different pedigree (not shown). The affected colt in the pedigree appeared normal at birth, and exhibited well developed musculature, although he had an audible inspiratory noise when restrained. Endoscopy was performed on the colt which revealed intermittent upper airway obstruction due to paralysis of the pharyngeal and laryngeal muscles. The colt displayed 3 spontaneous episodes of HYPP within the first 5 months of its life. By contrast, in most horses with HYPP spontaneous episodes of HYPP are not observed until a later age, usually 3 years, which clearly showed that this homozygous horse was more severely affected with the disease. Homozygosity for dominant HYPP does not appear to be life threatening for the afflicted horse.

Figure 4:
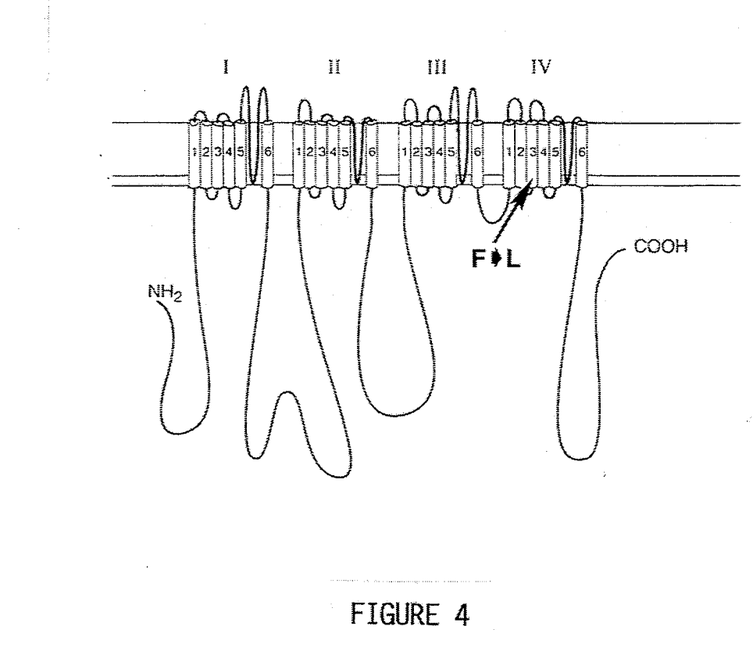
FIG. 4 is a schematic diagram showing localization of the HYPP horse mutation in the adult skeletal muscle sodium channel α subunit gene protein product.

In the HYPP horses described in this study, the membrane potential of affected muscle has been shown to be reduced, and this abnormality is exacerbated by increasing extracellular potassium. See, Spier, S. J., et al., *J. Am. Vet. Med. Assoc.* (In press) 202:993 (1993). The domain IV-$S_3$ Phe→ Leu mutation that has been identified by this invention in affected horse sodium channel is believed to lie in a transmembrane domain near the cytoplasmic face of the membrane as illustrated in FIG. 4. The two mutations recently shown to cause HYPP in humans also lie near the cytoplasmic surface of the membrane, however they are in different domains of the protein (Domaine IV $S_6$ Met→ Val (See, Koch, M. C., et al., *Hum. Genet.* 88:71 (1991)); Domaine II $S_5$ Thr→ Met (See, Ptacek, L. J., et al., *Am J. Hum. Genet.* 49:851 (1991)). All three mutations are relatively conservative amino acid substitutions of a highly conserved residue in a transmembrane domain; all cause potassium-induced paralysis that is preceded or associated with myotonia. Only a single human mutation (IV $S_6$ Met→ Val) has been correlated with specific channel gating abnormalities at the single channel level. See, Cannon, S. C., et al., *Neuron* 6:619 (1991), the disclosure of which is incorporated herein by reference. This mutation causes a non-inactivating mode of gating which is exacerbated by increasing extracellular potassium.

The present invention is not limited to the methods specifically illustrated herein. Specifically, any method that is capable of detecting and/or showing the Phenylalanine to Leucine base change identified herein in the horse adult skeletal muscle sodium channel gene, domain IV, transmembrane segment $S_3$ is encompassed within the present invention. For example, chemical cleavage, RNAse digestion, heteroduplex mapping, SSCP, ASOH, and RFLP may all be used to detect the mutation identified herein as well as any other methods capable of performing the same function.

Although the invention has been described in detail for the purposes of illustration, it is to be understood that such detail is solely for that purpose and that variations can be made therein by those skilled in the art without departing from the spirit and scope of the invention except as it may be limited by the claims.

---

We claim:

1. A method for detecting the genetic mutation in horses that causes hyperkalaemic periodic paralysis (HYPP) wherein said mutation is in the horse adult skeletal muscle sodium channel alpha subunit gene, domain IV, segment S3, said method comprising:
  obtaining genomic DNA or RNA from a fetus, living, or deceased horse;
  amplifying said DNA or reverse transcribed RNA; and
  detecting the presence or absence of a mutation consisting of a C to G single base change in said gene, wherein the DNA sequence of said gene in HYPP-affected horses consists of 5'-AACATCTTGGACTTCGT (SEQ ID NO: 2) and the corresponding DNA sequence in nonaffected horses consists of 5'-AACATCTTCGACTTCGT (SEQ ID NO: 1).

2. The method of claim 1, wherein the mutation is detected by allele-specific oligonucleotide hybridization.

3. The method of claim 1, wherein the mutation is detected by single-strand conformer polymorphism analysis.

4. The method of claim 1, wherein the mutation is detected by restriction fragment length polymorphism analysis after digestion of the amplification product with an enzyme that recognizes the Taq I restriction enzyme site.

5. A method of detecting the mutation in the horse adult muscle sodium channel alpha subunit gene of horses that causes hyperkalaemic periodic paralysis (HYPP), comprising:
  obtaining genomic DNA or RNA from a fetus, living, or deceased horse;
  amplifying said DNA or reverse transcribed RNA by polymerase chain reaction; and
  detecting a mutation consisting of a C to G single base change in said gene, wherein the DNA sequence of said gene in HYPP-affected horses consists of 5'-AACATCTTGGACTTCGT (SEQ ID NO: 2) and the corresponding DNA sequence in nonaffected horses consists of 5'-AACATCTTCGACTTCGT (SEQ ID NO: 1) that results in substitution of a leucine amino acid residue for a phenylalanine amino acid residue in the transcription products of domain IV, transmembrane region S3 of the sodium channel alpha subunit genes in HYPP-affected horses as compared to normal horses, respectively, by allele-specific oligonucleotide hybridization of olionucleotide probes to said amplified DNA.

6. The method of claim 5 wherein said oligonucleotide probes consist of:
  Normal Horse: 5'-AACATCTTCGACTTCGT (SEQ ID NO: 1) and
  HYPP Horse: 5'-AACATCTTGGACTTCGT (SEQ ID NO: 2).

7. A method of detecting the mutation in the horse adult skeletal muscle sodium channel alpha subunit gene that causes hyperkalaemic periodic paralysis (HYPP), comprising:

obtaining genomic DNA or RNA from a fetus, living, or deceased horse;

amplifying the genomic DNA or reverse transcribed RNA by polymerase chain reaction employing the primers:

Horse IVS$_2$F4: 5'-GGGGAGTGTGTGCTCAAGATG (SEQ ID NO: 3) and

Horse IVS$_3$R: 5'-AATGGACAGGATGACAACCAC (SEQ ID NO: 4)

to obtain an amplification product that includes part of the horse adult skeletal muscle sodium channel alpha subunit gene defined as domain IV segment S$_3$; and analyzing said product for said mutation which consists of a C to G single base change in said gene, wherein the DNA sequence of said gene in HYPP-affected horses consists of 5'-AACATCTTGGACTTCGT (SEQ ID NO: 2) and the corresponding DNA sequence in nonaffected horses consists of 5'-AACATCTTCGACTTCGT (SEQ ID NO: 1).

8. The method of claim 7 wherein said analysis of the amplification product employs allele-specific hybridization using oligonucleotide probes complementary to the horse adult skeletal muscle sodium channel alpha subunit gene defined as domain IV segment S$_3$.

9. The method of claim 8, wherein said oligonucleotide probes comprise:

Normal Horse: 5'-AACATCTTCGACTTCGT (SEQ ID NO: 1) and

HYPP Horse: 5'-AACATCTTGGACTTCGT (SEQ ID NO): 2).

10. The method of claim 7, wherein said analysis of the amplification product employs restriction fragment length polymorphism analysis after digestion of the amplification product with an enzyme that recognizes the Taq I restriction enzyme site.

11. Purified and isolated nucleotide sequences consisting of nucleotide sequences encoding part of the horse adult skeletal muscle sodium channel alpha subunit gene defined as domain IV segment S$_3$ consisting of the nucleotide sequences:

5'-AACATCATTGGACTT (SEQ ID NO: 2) and
5'-AACATCTTCGATTCGT (SEQ ID NO: 1).

12. A kit for detecting the mutation in the horse adult skeletal muscle sodium channel alpha subunit gene that causes hyperkalaemic periodic paralysis, comprising amplification primers, wherein said primers consist of:

Horse IVS$_2$F4: 5'-GGGGAGTGTGTGCTCAAGATG (SEQ ID NO: 3) and

Horse IVS$_3$R: 5'-AATGGACAGGATGACAACCAC (SEQ ID NO: 4).

13. The kit of claim 12, further comprising oligonucleotide probes that consist of:

Normal Horse: 5'-AACATCTTCGACTTCGT (SEQ ID NO: 1)and

HYPP Horse: 5'-AACATCTTGGACTTCGT (SEQ ID NO: 2).

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 17 nucleotides
        ( B ) TYPE: nucleic acid
        ( C ) STRANDEDNESS: double
        ( D ) TOPOLOGY: linear     ( i i ) MOLECULE TYPE: genomic DNA     ( i i i ) HYPOTHETICAL: yes     ( i v ) ANTI-SENSE: no     ( v i ) ORIGINAL SOURCE: muscle mRNA
        ( A ) ORGANISM: horse
        ( B ) STRAIN: Quarter Horse
        ( C ) INDIVIDUAL ISOLATE: normal horse
        ( E ) HAPLOTYPE: normal horse
        ( F ) TISSUE TYPE: adult skeletal muscle
        ( G ) CELL TYPE: myofiber     ( i x ) FEATURE:
        ( A ) NAME/KEY: normal sequence region of horse sodium
            channel gene overlapping mutation causing hyperkaelemic
            periodic paralysis
        ( B ) LOCATION: domain IV, region S3
        ( C ) IDENTIFICATION METHOD: cross- species RT-PCR using
            previously described rat and human sequences
        ( D ) OTHER INFORMATION: complete horse sequence not
            known; corresponds to nucleotides of human sequence     ( x ) PUBLICATION INFORMATION:
        ( A ) AUTHORS: Rudolph, J.A.
            Spier, S.J.
            Byrns, G.
            Rojas, C.V.
            Bernoco, D.
            Hoffman, E.P.
        ( B ) TITLE: Periodic Paralysis In Quarter Horses: A
            Sodium Channel Mutation Disseminated By Selective Breeding
(C) JOURNAL: Nature Genetics
(D) VOLUME: 2
(F) PAGES: 144-147
(G) DATE: 1992
(K) RELEVANT RESIDUES IN SEQ ID NO: 1: 1 to 17

(x i) SEQUENCE DESCRIPTION: SEQ ID NO: 1:

AAC ATC TTC GAC TTC GT 17

(2) INFORMATION FOR SEQ ID NO:2:

(i) SEQUENCE CHARACTERISTICS:
(A) LENGTH: 17 nucleotides
(B) TYPE: nucleic acid
(C) STRANDEDNESS: double
(D) TOPOLOGY: linear (i i) MOLECULE TYPE: genomic DNA (i i i) HYPOTHETICAL: yes (i v) ANTI-SENSE: no (v i) ORIGINAL SOURCE: muscle mRNA
(A) ORGANISM: horse
(B) STRAIN: Quarter Horse
(F) TISSUE TYPE: adult skeletal muscle
(G) CELL TYPE: myofiber (i x) FEATURE:
(A) NAME/KEY: sequence of horse sodium channel gene
containing mutation causing hyperkaelemic periodic
paralysis
(B) LOCATION: domain IV, region S3
(C) IDENTIFICATION METHOD: cross- species RT-PCR using
previously described rat and human sequences
(D) OTHER INFORMATION: complete horse sequence not
known; corresponds to nucleotides of human sequence (x) PUBLICATION INFORMATION:
(A) AUTHORS: RUDOLPH, J.A.
SPIER, S.J.
BYRNS, G.
ROJAS, C.V.
BERNOCO, D.
HOFFMAN, E.P.
(B) TITLE: Periodic Paralysis In Quarter Horses: A
Sodium Channel Mutation Disseminated By Selective
Breeding
(C) JOURNAL: Nature Genetics
(D) VOLUME: 2
(F) PAGES: 144-147
(G) DATE: 1992
(K) RELEVANT RESIDUES IN SEQ ID NO: 2: From 1 to 17

(x i) SEQUENCE DESCRIPTION: SEQ ID NO: 2:

AAC ATC TTG GAC TTC GT 17

(2) INFORMATION FOR SEQ ID NO:3:

(i) SEQUENCE CHARACTERISTICS:
(A) LENGTH: 21 base pairs
(B) TYPE: nucleic acid
(C) STRANDEDNESS: double
(D) TOPOLOGY: linear (i i) MOLECULE TYPE: genomic DNA (i i i) HYPOTHETICAL: yes (i v) ANTI-SENSE: no (v i) ORIGINAL SOURCE: muscle mRNA
(A) ORGANISM: horse
(B) STRAIN: Quarter Horse
(D) DEVELOPMENTAL STAGE: 2 years
(F) TISSUE TYPE: adult skeletal muscle (G) CELL TYPE: myofiber (ix) FEATURE:
                (A) NAME/KEY: sequence of a region of horse sodium
                        channel gene flanking mutation causing periodic paralysis
                (B) LOCATION: domain IV, region S2
                (C) IDENTIFICATION METHOD: cross species RT-PCR using
                        rat and human sequences
                (D) OTHER INFORMATION: complete horse sequence unknown;
                        corresponds to nucleotides of human sequence (x) PUBLICATION INFORMATION:
                (A) AUTHORS: Rudolph, J.A.
                        Spier, S.J.
                        Byrns, G.
                        Rojas, C.V.
                        Bernoco, D.
                        Hoffman, E.P.
                (B) TITLE: Periodic Paralysis In Quarter Horses: A
                        Sodium Channel Mutation Disseminated By Selective
                        Breeding
                (C) JOURNAL: Nature Genetics
                (D) VOLUME: 2
                (F) PAGES: 144-147
                (G) DATE: 1992
                (K) RELEVANT RESIDUES IN SEQ ID NO: 3: From 1 to 21

(xi) SEQUENCE DESCRIPTION: SEQ ID NO: 3:

GGGGAGTGTG TGCTCAAGAT G                                   21

(2) INFORMATION FOR SEQ ID NO:4:

(i) SEQUENCE CHARACTERISTICS:
                (A) LENGTH: 21 nucleotides
                (B) TYPE: nucleic acid
                (C) STRANDEDNESS: double
                (D) TOPOLOGY: linear (ii) MOLECULE TYPE: genomic DNA (iii) HYPOTHETICAL: yes (iv) ANTI-SENSE: yes (vi) ORIGINAL SOURCE: muscle mRNA
                (A) ORGANISM: horse
                (B) STRAIN: Quarter Horse
                (D) DEVELOPMENTAL STAGE: 1 year
                (F) TISSUE TYPE: adult skeletal muscle
                (G) CELL TYPE: myofiber (ix) FEATURE:
                (A) NAME/KEY: sequence of a region of horse sodium
                        channel gene flanking mutation causing periodic paralysis
                (B) LOCATION: domain IV, region S3
                (C) IDENTIFICATION METHOD: cross species RT-PCR using
                        rat and human sequences
                (D) OTHER INFORMATION: complete horse sequence not
                        known; corresponds to nucleotides of human sequence (x) PUBLICATION INFORMATION:
                (A) AUTHORS: RUDOLPH, J.A.
                        SPIER, S.J.
                        BYRNS, G.
                        ROJAS, C.V.
                        BERNOCO, D.
                        HOFFMAN, E.P.
                (B) TITLE: Periodic Paralysis In Quarter Horses: A
                        Sodium Channel Mutation Disseminated By Selective
                        Breeding
                (C) JOURNAL: Nature Genetics
                (D) VOLUME: 2
                (F) PAGES: 144-147
                (G) DATE: 1992
                (K) RELEVANT RESIDUES IN SEQ ID NO: 4: From 1 to 21

(xi) SEQUENCE DESCRIPTION: SEQ ID NO: 4:

AATGGACAGG ATGACAACCA C                                   21

( 2 ) INFORMATION FOR SEQ ID NO:5:

( i ) SEQUENCE CHARACTERISTICS:
        ( A ) LENGTH: 13 nucleotides
        ( B ) TYPE: nucleic acid
        ( C ) STRANDEDNESS: double
        ( D ) TOPOLOGY: linear     ( i i ) MOLECULE TYPE: genomic DNA     ( i i i ) HYPOTHETICAL: yes     ( i v ) ANTI-SENSE: no     ( v i ) ORIGINAL SOURCE: muscle mRNA
        ( A ) ORGANISM: horse
        ( B ) STRAIN: Quarter Horse
        ( C ) INDIVIDUAL ISOLATE: normal horse
        ( E ) HAPLOTYPE: normal horse
        ( F ) TISSUE TYPE: adult skeletal muscle
        ( G ) CELL TYPE: myofiber     ( i x ) FEATURE:
        ( A ) NAME/KEY: normal sequence region of horse sodium
                channel gene overlapping mutation causing hyperkaelemic
                periodic paralysis
        ( B ) LOCATION: domain IV, region S3
        ( C ) IDENTIFICATION METHOD: cross- species RT-PCR using
                previously described rat and human sequences
        ( D ) OTHER INFORMATION: complete horse sequence not
                known; corresponds to nucleotides of human sequence     ( x ) PUBLICATION INFORMATION:
        ( A ) AUTHORS: Rudolph, J.A.
                Spier, S.J.
                Byrns, G.
                Rojas, C.V.
                Bernoco, D.
                Hoffman, E.P.
        ( B ) TITLE: Periodic Paralysis In Quarter Horses: A
                Sodium Channel Mutation Disseminated By Selective
                Breeding
        ( C ) JOURNAL: Nature Genetics
        ( D ) VOLUME: 2
        ( F ) PAGES: 144-147
        ( G ) DATE: 1992
        ( K ) RELEVANT RESIDUES IN SEQ ID NO: 5: 1 to 13

( x i ) SEQUENCE DESCRIPTION: SEQ ID NO: 5:

C  ATC  TTC  GAC  TTC                13
          Ile  Phe  Asp  Phe ( 2 ) INFORMATION FOR SEQ ID NO:6:

( i ) SEQUENCE CHARACTERISTICS:
        ( A ) LENGTH: 4 amino acids
        ( B ) TYPE: amino acid
        ( D ) TOPOLOGY: linear     ( i i ) MOLECULE TYPE: peptide     ( i i i ) HYPOTHETICAL: yes     ( v i ) ORIGINAL SOURCE: muscle mRNA
        ( A ) ORGANISM: horse
        ( B ) STRAIN: Quarter Horse
        ( C ) INDIVIDUAL ISOLATE: normal horse
        ( E ) HAPLOTYPE: normal horse
        ( F ) TISSUE TYPE: adult skeletal muscle
        ( G ) CELL TYPE: myofiber     ( i x ) FEATURE:
        ( A ) NAME/KEY: normal sequence region of horse sodium
                channel gene overlapping mutation causing hyperkaelemic
                periodic paralysis
        ( B ) LOCATION: domain IV, region S3
        ( C ) IDENTIFICATION METHOD: cross- species RT-PCR using
                previously described rat and human sequences
        ( D ) OTHER INFORMATION: complete horse sequence not known; corresponds to nucleotides of human sequence ( x ) PUBLICATION INFORMATION:
  ( A ) AUTHORS: Rudolph, J.A.
    Spier, S.J.
    Byrns, G.
    Rojas, C.V.
    Bernoco, D.
    Hoffman, E.P.
  ( B ) TITLE: Periodic Paralysis In Quarter Horses: A
    Sodium Channel Mutation Disseminated By Selective
    Breeding
  ( C ) JOURNAL: Nature Genetics
  ( D ) VOLUME: 2
  ( F ) PAGES: 144-147
  ( G ) DATE: 1992
  ( K ) RELEVANT RESIDUES IN SEQ ID NO: 6: 1 to 4

( x i ) SEQUENCE DESCRIPTION: SEQ ID NO: 6:

Ile Phe Asp Phe ( 2 ) INFORMATION FOR SEQ ID NO:7:

( i ) SEQUENCE CHARACTERISTICS:
  ( A ) LENGTH: 13 nucleotides
  ( B ) TYPE: nucleic acid
  ( C ) STRANDEDNESS: double
  ( D ) TOPOLOGY: linear  ( i i ) MOLECULE TYPE: genomic DNA  ( i i i ) HYPOTHETICAL: yes  ( i v ) ANTI-SENSE: no  ( v i ) ORIGINAL SOURCE: muscle mRNA
  ( A ) ORGANISM: horse
  ( B ) STRAIN: Quarter Horse
  ( F ) TISSUE TYPE: adult skeletal muscle
  ( G ) CELL TYPE: myofiber  ( i x ) FEATURE:
  ( A ) NAME/KEY: sequence of horse sodium channel gene
    containing mutation causing hyperkaelemic periodic
    paralysis
  ( B ) LOCATION: domain IV, region S3
  ( C ) IDENTIFICATION METHOD: cross- species RT-PCR using
    previously described rat and human sequences
  ( D ) OTHER INFORMATION: complete horse sequence not
    known; corresponds to nucleotides of human sequence  ( x ) PUBLICATION INFORMATION:
  ( A ) AUTHORS: RUDOLPH, J.A.
    SPIER, S.J.
    BYRNS, G.
    ROJAS, C.V.
    BERNOCO, D.
    HOFFMAN, E.P.
  ( B ) TITLE: Periodic Paralysis In Quarter Horses: A
    Sodium Channel Mutation Disseminated By Selective
    Breeding
  ( C ) JOURNAL: Nature Genetics
  ( D ) VOLUME: 2
  ( F ) PAGES: 144-147
  ( G ) DATE: 1992
  ( K ) RELEVANT RESIDUES IN SEQ ID NO: 7: From 1 to 13

( x i ) SEQUENCE DESCRIPTION: SEQ ID NO: 7:

C ATC TTG GAC TTC           13
   Ile Leu Asp Phe ( 2 ) INFORMATION FOR SEQ ID NO:8:

( i ) SEQUENCE CHARACTERISTICS:
  ( A ) LENGTH: 4 amino acids
  ( B ) TYPE: amino acid
  ( D ) TOPOLOGY: linear (ii) MOLECULE TYPE: peptide (iii) HYPOTHETICAL: yes (iv) ANTI-SENSE: no (vi) ORIGINAL SOURCE: muscle mRNA
  (A) ORGANISM: horse
  (B) STRAIN: Quarter Horse
  (F) TISSUE TYPE: adult skeletal muscle
  (G) CELL TYPE: myofiber (ix) FEATURE:
  (A) NAME/KEY: sequence of horse sodium channel gene
        containing mutation causing hyperkaelemic periodic
        paralysis
  (B) LOCATION: domain IV, region S3
  (C) IDENTIFICATION METHOD: cross-species RT-PCR using
        previously described rat and human sequences
  (D) OTHER INFORMATION: complete horse sequence not
        known; corresponds to nucleotides of human sequence (x) PUBLICATION INFORMATION:
  (A) AUTHORS: RUDOLPH, J.A.
        SPIER, S.J.
        BYRNS, G.
        ROJAS, C.V.
        BERNOCO, D.
        HOFFMAN, E.P.
  (B) TITLE: Periodic Paralysis In Quarter Horses: A
        Sodium Channel Mutation Disseminated By Selective
        Breeding
  (C) JOURNAL: Nature Genetics
  (D) VOLUME: 2
  (F) PAGES: 144-147
  (G) DATE: 1992
  (K) RELEVANT RESIDUES IN SEQ ID NO: 8: From 1 to 4

(xi) SEQUENCE DESCRIPTION: SEQ ID NO: 8:

Ile Leu Asp Phe